United States Patent [19]

Knight

[11] Patent Number: 5,797,401
[45] Date of Patent: Aug. 25, 1998

[54] POST SURGICAL PENIS PROTECTOR APPLIANCE

[76] Inventor: Lila C. Knight, 940 Warren Morrow Rd., Lawrenceville, Ga. 30243

[21] Appl. No.: 847,458

[22] Filed: Apr. 24, 1997

[51] Int. Cl.$^6$ ............................................. A61F 6/02
[52] U.S. Cl. ................... 128/842; 602/67; 602/68; 602/69
[58] Field of Search .................. 128/842, 844, 128/918, 96.1–102.1; 602/67–73

[56] References Cited

U.S. PATENT DOCUMENTS

| | | |
|---|---|---|
| 4,526,167 | 7/1985 | Ebenal ............................ 128/158 |
| 5,274,854 | 1/1994 | Wenner et al. ..................... 2/403 |
| 5,379,462 | 1/1995 | Morgan et al. .................... 2/403 |
| 5,547,466 | 8/1996 | McRoberts et al. ................ 602/70 |

*Primary Examiner*—Michael A. Brown
*Attorney, Agent, or Firm*—Joseph N. Breaux

[57] ABSTRACT

A post surgical penis protector appliance including an attachment belt securable about the waist of a user; a shield support constructed from a length of a formable strand material secured to and extending from the attachment belt, the shield support including two drawstring attachment notches; and a fabric shield constructed in the shape of a bag, the bag having a drawstring closure mechanism including a drawstring positioned around the perimeter of an insertion opening thereof, the fabric shield defining a compartment therein sized to receive at least a portion of the shield support, the drawstring attachment notches being positioned on the length of formable strand material in a manner such that the drawstring of the drawstring mechanism is positionable in registration with the attachment notches when a portion of the shield support is positioned into the compartment.

20 Claims, 2 Drawing Sheets

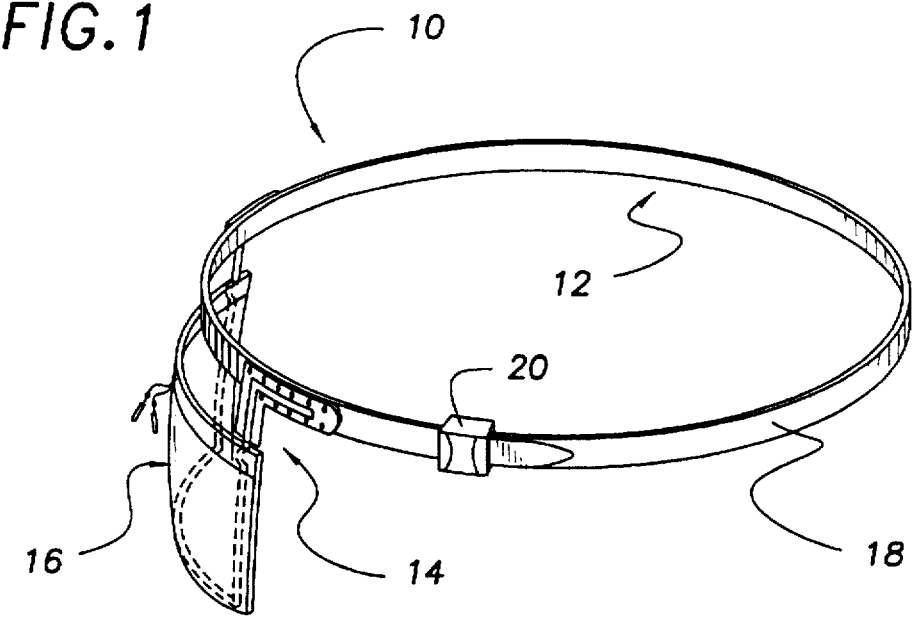
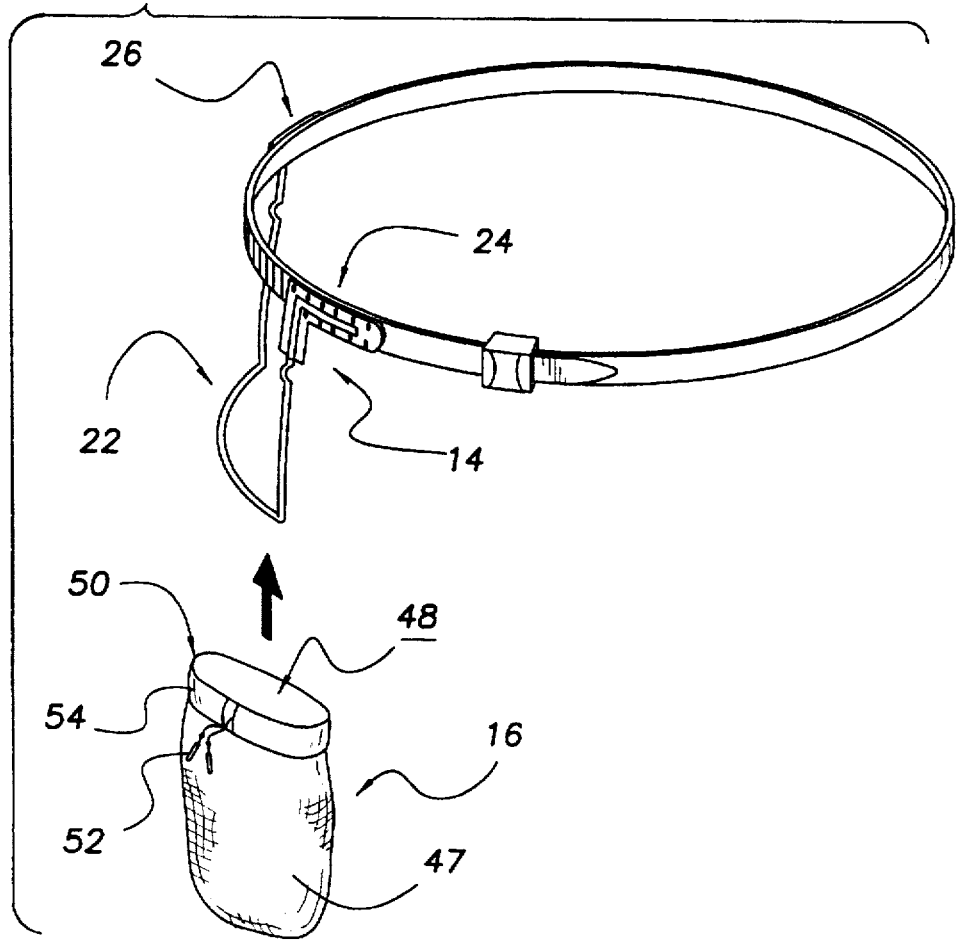

POST SURGICAL PENIS PROTECTOR APPLIANCE

TECHNICAL FIELD

The present invention relates to protective devices and appliances for protecting areas of the body after surgery and more particularly to a post surgical penis protector appliance that includes an attachment belt securable about the waist of a user; a shield support constructed from a length of a formable strand material secured to and extending from the attachment belt, the shield support including two drawstring attachment notches; and a fabric shield constructed in the shape of a bag, the bag having a drawstring closure mechanism including a drawstring positioned around the perimeter of an insertion opening thereof, the fabric shield defining a compartment therein sized to receive at least a portion of the shield support, the drawstring attachment notches being positioned on the length of formable strand material in a manner such that the drawstring of the drawstring mechanism is positionable in registration with the attachment notches when a portion of the shield support is positioned into the compartment.

BACKGROUND OF THE INVENTION

It is important to protect any area upon which surgery has been performed from unnecessary contact to minimize complications after surgery. It would be a benefit, therefore, to have a protective appliance for shielding and protecting the penis after surgical procedures such as circumcisions have been performed. Because the penis is enclosed in clothing when the patient is in public, it would be a benefit, to have a protective appliance that could be worn in a relatively unnoticeable manner that included a shielding structure that would hold the clothing of the wearer away from the penis. Because the shield can become soiled with perspiration and urine while being worn, it would be a further benefit to have a shield that could be supported on a shield support that could be replaced when desired.

SUMMARY OF THE INVENTION

It is thus an object of the invention to provide a post surgical penis protector appliance.

It is a further object of the invention to provide a post surgical penis protector appliance can be worn by a patient in a relatively unnoticeable manner.

It is a still further object of the invention to provide a post surgical penis protector appliance that includes a shielding structure for holding the clothing of the wearer away from the penis.

It is a still further object of the invention to provide a post surgical penis protector appliance that includes a shield that is supported on a shield support and that can be replaced when desired.

It is a still further object of the invention to provide a post surgical penis protector appliance that includes an attachment belt securable about the waist of a user; a shield support constructed from a length of a formable strand material secured to and extending from the attachment belt, the shield support including two drawstring attachment notches; and a fabric shield constructed in the shape of a bag, the bag having a drawstring closure mechanism including a drawstring positioned around the perimeter of an insertion opening thereof, the fabric shield defining a compartment therein sized to receive at least a portion of the shield support, the drawstring attachment notches being positioned on the length of formable strand material in a manner such that the drawstring of the drawstring mechanism is positionable in registration with the attachment notches when a portion of the shield support is positioned into the compartment.

It is a still further object of the invention to provide a post surgical penis protector appliance that accomplishes some or all of the above objects in combination.

Accordingly, a post surgical penis protector appliance is provided. The penis protector appliance includes an attachment belt securable about the waist of a user; a shield support constructed from a length of a formable strand material secured to and extending from the attachment belt, the shield support including two drawstring attachment notches; and a fabric shield constructed in the shape of a bag, the bag having a drawstring closure mechanism including a drawstring positioned around the perimeter of an insertion opening thereof, the fabric shield defining a compartment therein sized to receive at least a portion of the shield support, the drawstring attachment notches being positioned on the length of formable strand material in a manner such that the drawstring of the drawstring mechanism is positionable in registration with the attachment notches when a portion of the shield support is positioned into the compartment. The term "formable strand material" is used herein to mean a material such as a wire or a thin plastic member.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is a perspective view of an exemplary embodiment of the post surgical penis protector appliance of the present invention showing the leather attachment belt, the wire shield support secured to the leather attachment belt, and the fabric shield with drawstring attachment mechanism positioned onto the wire shield support.

FIG. 2 is a second perspective view of the exemplary embodiment of the post surgical penis protector appliance of FIG. 1 showing the leather attachment belt with the wire shield support secured thereto and the fabric shield with drawstring attachment mechanism exploded away from the wire shield support showing the insertion opening and the draw string mechanism.

DESCRIPTION OF THE EXEMPLARY EMBODIMENT

Figure 3:
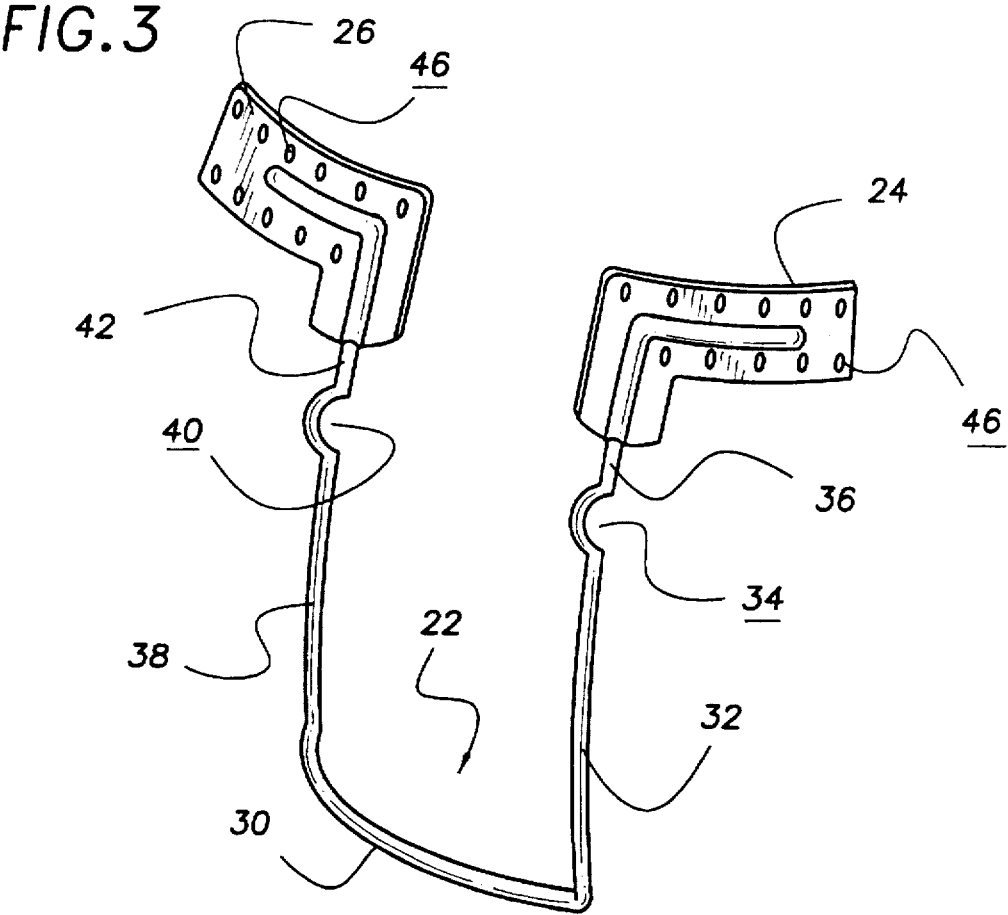
FIG. 3 is a perspective view of the wire shield support in isolation showing the left and right belt mounting plates, the bent wire shield support member and the two fabric shield attachment notches.

FIG. 1 shows an exemplary embodiment of the post surgical penis protector appliance of the present invention generally designated by the numeral 10. Protector appliance 10 includes an attachment belt assembly, generally designated 12; a shield support assembly, generally designated 14; and a fabric shield, generally designated 16. In this embodiment attachment belt assembly 12 includes a leather belt member 18 having a conventional plastic buckle assembly 20 provided at one end thereof. Leather belt member 18 is of a length sufficient to allow securement of belt assembly 12 about the waist of a patient.

With reference now to FIG. 2, shield support assembly 14 includes a metal wire shield support member, generally designated 22; and left and right belt mounting plates, generally designated 24,26. With reference now to FIG. 3, in this embodiment metal wire shield support member 22 is constructed of stainless steel wire that has been bent to include a centrally positioned curved bottom portion 30; a curved left vertical member 32 having a left drawstring attachment notch 34 and a right angle bent left plate attachment portion 36 installed within left belt mounting plate 24; and a curved right vertical member 38 having a right drawstring attachment notch 40 and a right angle bent right plate attachment portion 42 mounted within right belt mounting plate 26. Left and right belt mounting plates 24,26 are of molded plastic construction. Each left and right belt mounting plate 24,26 includes a number of mounting apertures 46 that are used to stitch or rivet left and right mounting plates 24,26 to leather attachment belt 18. Although stitching and riveting are specifically mentioned methods of securing mounting plates 24,26 to attachment belt 18 any suitable attachment method can be used if desired.

With reference back to FIG. 2, in this embodiment fabric shield 16 is constructed from cotton fabric that has been sewn into the shape of a bag/sleeve 47 having an insertion opening 48 defined by a perimeter edge having a drawstring attachment mechanism 50 provided thereon. In this embodiment drawstring attachment mechanism 50 includes a drawstring 52 installed within a sewn hem 54.

Figure 4:
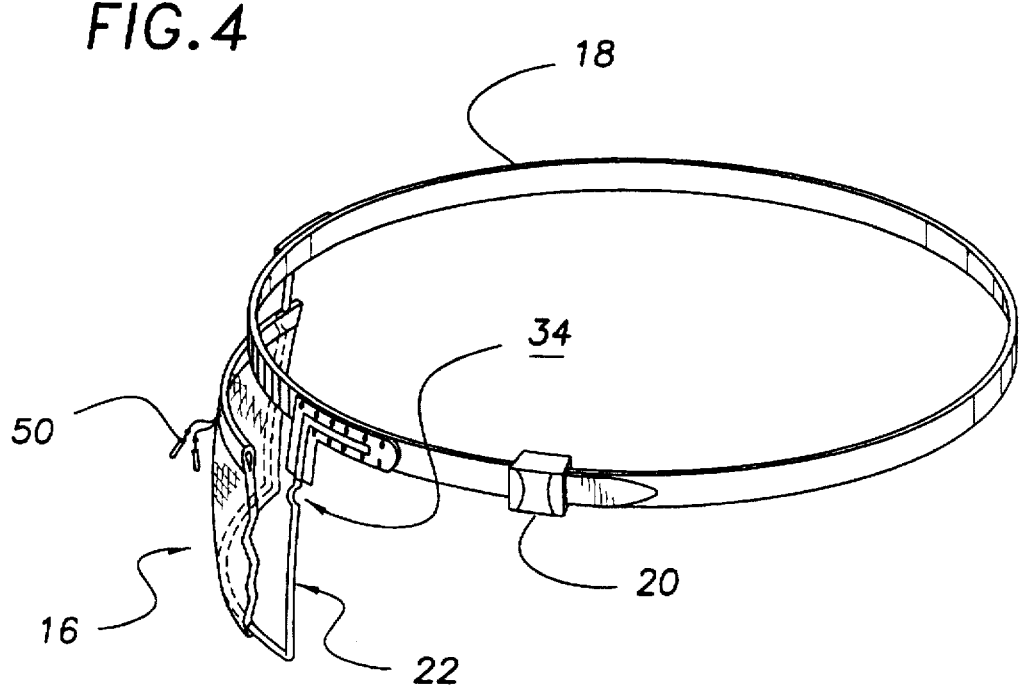
FIG. 4 is a partial cutaway, perspective view of the exemplary embodiment of the post surgical penis protector appliance of FIG. 1 showing the fabric shield installed onto the wire shield support with a portion of the fabric shield cut away to show a portion of the wire shield.

With reference to FIG. 4, prior to use fabric shield 16 is positioned onto and over a portion of metal wire shield support member 22 in a manner such that drawstring 50 is placed in registration with drawstring attachment notches 34,40 (attachment notch 40 shown in 3), and drawstring 50 tightened to secure fabric shield 16 to shield support member 22. Leather attachment belt 18 is then positioned about the waist of the user in a manner such that fabric shield 16 is positioned over the penis of the user and secured by operation of plastic buckle 20. Should fabric shield 16 become soiled it is removed by reversing the previous steps and a new clean fabric shield 16 attached as described. Although shield support member 20 can be formed from rigid materials, in this embodiment shield support member 22 is formed from stainless steel wire of a gauge that allows the user to bend shield support member 22 to conform to the body of the user.

It can be seen from the preceding description that a post surgical penis protector appliance has been provided that can be worn by a patient in a relatively unnoticeable manner; that includes a shielding structure for holding the clothing of the wearer away from the penis; that includes a shield that is supported on a shield support and that can be replaced when desired; and that includes an attachment belt securable about the waist of a user; a shield support constructed from a length of a formable strand material secured to and extending from the attachment belt, the shield support including two drawstring attachment notches; and a fabric shield constructed in the shape of a bag, the bag having a drawstring closure mechanism including a drawstring positioned around the perimeter of an insertion opening thereof, the fabric shield defining a compartment therein sized to receive at least a portion of the shield support, the drawstring attachment notches being positioned on the length of formable strand material in a manner such that the drawstring of the drawstring mechanism is positionable in registration with the attachment notches when a portion of the shield support is positioned into the compartment.

It is noted that the embodiment of the post surgical penis protector appliance described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A post surgical penis protector appliance comprising:

an attachment belt securable about a waist of a user;

a shield support constructed from a length of a formable strand material secured to and extending from said attachment belt, said shield support including a left and a right drawstring attachment notches, said shield support being affixed to said attachment belt; and a fabric shield constructed in a bag shape, said fabric shield having a drawstring closure mechanism including a drawstring positioned around a perimeter of an insertion opening thereof, said fabric shield defining a compartment therein sized to receive at least a portion of said shield support;

said left and right drawstring attachment notches of said shield support being positioned on said length of formable strand material in a manner such that said drawstring of said drawstring mechanism is positionable in registration with said attachment notches when a portion of said shield support is positioned into said compartment.

2. The post surgical penis protector appliance of claim 1, wherein:

said formable strand material is metal wire.

3. The post surgical penis protector appliance of claim 2, wherein:

said metal wire is formable by a user.

4. The post surgical penis protector appliance of claim 2 wherein:

said fabric shield is constructed from cotton fabric.

5. The post surgical penis protector appliance of claim 2 wherein:

said attachment belt is constructed from leather and includes a buckle assembly provided at one end thereof.

6. The post surgical penis protector appliance of claim 2 wherein:

said shield support includes a shield support member and a left and a right belt mounting plate.

7. The post surgical penis protector appliance of claim 6 wherein:

said shield support member includes a centrally positioned curved bottom portion; a curved left vertical member having said left drawstring attachment notch formed therein and a right angle bent left plate attachment portion installed within said left belt mounting plate; and a curved right vertical member having said right drawstring attachment notch formed therein and a right angle bent right plate attachment portion mounted within said right belt mounting plate.

8. The post surgical penis protector appliance of claim 7, wherein:

said left and right belt mounting plates are of molded plastic construction and each includes a plurality of mounting apertures formed therethrough.

9. The post surgical penis protector appliance of claim 6, wherein:

said left and right belt mounting plates are of molded plastic construction and each includes a plurality of mounting apertures formed therethrough.

10. The post surgical penis protector appliance of claim 1 wherein:

said fabric shield is constructed from cotton fabric.

11. The post surgical penis protector appliance of claim 10 wherein:

said attachment belt is constructed from leather and includes a buckle assembly provided at one end thereof.

12. The post surgical penis protector appliance of claim 10 wherein:

said shield support includes a shield support member and a left and a right belt mounting plate.

13. The post surgical penis protector appliance of claim 12 wherein:

said shield support member includes a centrally positioned curved bottom portion; a curved left vertical member having said left drawstring attachment notch formed therein and a right angle bent left plate attachment portion installed within said left belt mounting plate; and a curved right vertical member having said right drawstring attachment notch formed therein and a right angle bent right plate attachment portion mounted within said right belt mounting plate.

14. The post surgical penis protector appliance of claim 1 wherein:

said attachment belt is constructed from leather and includes a buckle assembly provided at one end thereof.

15. The post surgical penis protector appliance of claim 14 wherein:

said shield support includes a shield support member and a left and a right belt mounting plate.

16. The post surgical penis protector appliance of claim 15 wherein:

said shield support member includes a centrally positioned curved bottom portion; a curved left vertical member having said left drawstring attachment notch formed therein and a right angle bent left plate attachment portion installed within said left belt mounting plate; and a curved right vertical member having said right drawstring attachment notch formed therein and a right angle bent right plate attachment portion mounted within said right belt mounting plate.

17. The post surgical penis protector appliance of claim 1 wherein:

said shield support includes a shield support member and a left and a right belt mounting plate.

18. The post surgical penis protector appliance of claim 17 wherein:

said shield support member includes a centrally positioned curved bottom portion; a curved left vertical member having said left drawstring attachment notch formed therein and a right angle bent left plate attachment portion installed within said left belt mounting plate; and a curved right vertical member having said right drawstring attachment notch formed therein and a right angle bent right plate attachment portion mounted within said right belt mounting plate.

19. The post surgical penis protector appliance of claim 18, wherein:

said left and right belt mounting plates are of molded plastic construction and each includes a plurality of mounting apertures formed therethrough.

20. The post surgical penis protector appliance of claim 17, wherein:

said left and right belt mounting plates are of molded plastic construction and each includes a plurality of mounting apertures formed therethrough.

* * * * *